United States Patent

Tomioka et al.

[11] Patent Number: 5,153,215
[45] Date of Patent: Oct. 6, 1992

[54] 1-PHENYLIMIDAZOLE DERIVATIVE AND ITS USE

[75] Inventors: Hiroki Tomioka, Toyonaka; Noriyasu Sakamoto, Nishinomiya; Kimitoshi Umeda; Hiroaki Fujimoto, both of Toyonaka; Takao Ishiwatari, Minoo; Hirosi Kisida, Takarazuka, all of Japan

[73] Assignee: Sumitomo Chemical Company, Limited, Osaka, Japan

[21] Appl. No.: 658,326

[22] Filed: Feb. 20, 1991

[30] Foreign Application Priority Data

Jun. 29, 1990 [JP] Japan .................. 2-173135
Sep. 4, 1990 [JP] Japan .................. 2-235439

[51] Int. Cl.$^5$ .................. A01N 43/50; C07D 233/64
[52] U.S. Cl. .................. 514/396; 514/399; 548/343.1
[58] Field of Search .................. 548/341, 342; 514/399, 514/396

[56] References Cited

U.S. PATENT DOCUMENTS

| | | | |
|---|---|---|---|
| 3,868,458 | 2/1975 | Baker et al. | 424/273 |
| 3,940,484 | 2/1976 | Baker et al. | 424/428 |
| 3,996,366 | 12/1976 | Baker et al. | 424/273 |
| 4,048,188 | 9/1977 | Baker et al. | 548/341 |
| 4,786,312 | 11/1988 | Schmierer et al. | 71/92 |

FOREIGN PATENT DOCUMENTS 0253310 1/1988 European Pat. Off. .
0396427 5/1990 European Pat. Off. .

Primary Examiner—Patricia L. Morris
Attorney, Agent, or Firm—Stevens, Davis, Miller & Mosher

[57] ABSTRACT

A novel 1-phenylimidazole derivative having the formula:

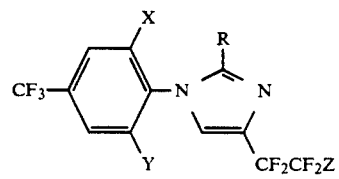

wherein R is a hydrogen atom or a methyl group; X is a fluorine atom, a chlorine atom or a nitro group; Y is a fluorine atom or a chlorine atom; Z is a hydrogen atom, a fluorine atom, a chlorine atom or a bromine atom, a process for producing the same and insecticides containing the same as an active ingredient, are disclosed.

24 Claims, No Drawings

1-PHENYLIMIDAZOLE DERIVATIVE AND ITS USE

BACKGROUND OF THE INVENTION

1. Field of the Invention

The present invention relates to a novel 1-phenylimidazole derivative having the formula [I]:

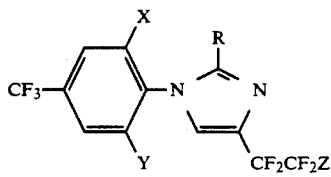

wherein R is a hydrogen atom or a methyl group; X is a fluorine atom, a chlorine atom or a nitro group; Y is a fluorine atom or a chlorine atom; Z is a hydrogen atom, a fluorine atom, a chlorine atom or a bromine atom, a process for producing the same and insecticides containing the same as an active ingredient.

2. Description of the Related Art

It is described in U.S. Pat. Nos. 3,868,458, 3,940,484 and U.S. Pat. No. 3,996,366 that a certain imidazole derivative is useful as an active ingredient of insecticide.

As a result of extensive investigations on compounds having an excellent insecticidal effect, the present inventors have found a 1-phenylimidazole derivative having the formula [I] exhibit an extremely high insecticidal effect, and thus have accomplished the present invention.

SUMMARY OF THE INVENTION

According to the present invention, there is provided a 1-phenylimidazole derivative having the formula [I]:

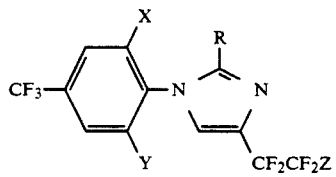

wherein R is a hydrogen atom or a methyl group; X is a fluorine atom, a chlorine atom or a nitro group; Y is a fluorine atom or a chlorine atom; Z is a hydrogen atom, a fluorine atom, a chlorine atom or a bromine atom, a process for producing the same and insecticides containing the same as an active ingredient.

The compounds of the present invention can be produced according to the following reaction scheme.

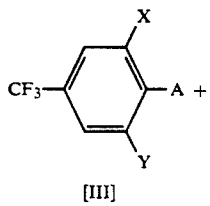

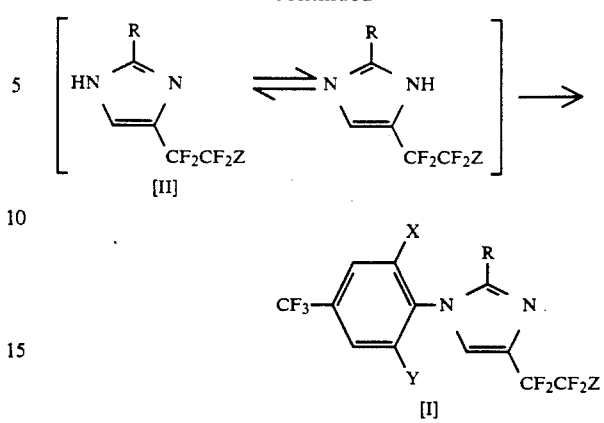

wherein R, X, Y and Z are each as defined above and A is a halogen atom.

The compound of the present invention can be produced by reacting halide compounds having the formula [III] with imidazole derivatives having the formula [II] at about −5° C. to about 150° C. for about 1 to 24 hours in a solvent in the presence of an reagent for removing a hydrogen halide.

The amounts of the reagents used in the reaction are 1-2 equivalents of the halide compounds having the formula [III] and 1-4 equivalents of the reagent for removing a hydrogen halide to one equivalent of the imidazole derivatives having the formula [II].

Examples of the solvent which is used for the both reactions described above include aliphatic hydrocarbons such as hexane, heptane, ligroin, petroleum ether, etc.; aromatic hydrocarbons such as benzene, toluene, xylene, etc.; halogenated hydrocarbons such as chloroform, carbon tetrachloride, dichloroethane, chlorobenzene, dichlorobenzene, etc.; ethers such as diethyl ether, diisopropyl ether, dioxan, tetrahydrofuran, ethylene glycol dimethyl ether, etc.; ketones such as acetone, methyl ethyl ketone, methyl isobutyl ketone, isophorone, cyclohexanone, etc.; esters such as ethyl acetate, butyl acetate, etc.; nitro compounds such as nitroethane, nitrobenzene, etc.; nitriles such as acetonitrile, isobutyronitrile, etc.; tertiary amines such as pyridine, triethylamine, N,N-diethylaniline, tributylamine, N-methylmorpholine, etc.; acid amides such as formamide, N,N-dimethylformamide, N,N-dimethylacetamide, etc.; sulfur compounds such as dimethylsulfoxide, sulfolane, etc.; or mixtures thereof.

Examples of the reagent of removing hydrogen halide include organic bases such as pyridine, triethylamine, N,N-diethylaniline, etc.; inorganic bases such as sodium hydroxide, potassium hydroxide, sodium carbonate, potassium carbonate, sodium hydrogen carbonate, calcium carbonate, sodium hydride, etc.; alkali metal alkoxides such as sodium methoxide, sodium ethoxide, etc.

After completion of the reaction, post-treatment follows in a conventional manner. If necessary and desired, the product may further be purified by chromatography, distillation, recrystallization, etc.

The imidazole derivatives having the formula [II] and the halide compounds having the formula [III] which are used as raw materials for the compounds of the present invention are prepared by the methods described in J. Org. Chem., 47, 2867 (1982), Japan Patent (laid open) 86-286,370 and U.S. Pat. Nos. 3,888,932, 3,928,416, European Patent 23,100, European Patent 34,402, British Patent 1,121,211 respectively, or in a manner similar to the methods.

Examples of the compounds of the present invention are shown in Table 1 below.

TABLE 1

[Structure: benzene ring with $CF_3$ at one position, X and Y substituents, connected via N to an imidazoline-type ring with R and $CF_2CF_2Z$]

| R | X | Y | Z |
|---|---|---|---|
| H | F | F | H |
| H | F | F | F |
| H | F | F | Cl |
| H | F | F | Br |
| H | F | Cl | H |
| H | F | Cl | F |
| H | F | Cl | Cl |
| H | F | Cl | Br |
| H | Cl | Cl | H |
| H | Cl | Cl | F |
| H | Cl | Cl | Cl |
| H | Cl | Cl | Br |
| H | $NO_2$ | F | H |
| H | $NO_2$ | F | F |
| H | $NO_2$ | F | Cl |
| H | $NO_2$ | F | Br |
| H | $NO_2$ | Cl | H |
| H | $NO_2$ | Cl | F |
| H | $NO_2$ | Cl | Cl |
| H | $NO_2$ | Cl | Br |
| $CH_3$ | F | F | H |
| $CH_3$ | F | F | F |
| $CH_3$ | F | F | Cl |
| $CH_3$ | F | F | Br |
| $CH_3$ | F | Cl | H |
| $CH_3$ | F | Cl | F |
| $CH_3$ | F | Cl | Cl |
| $CH_3$ | F | Cl | Br |
| $CH_3$ | Cl | Cl | H |
| $CH_3$ | Cl | Cl | F |
| $CH_3$ | Cl | Cl | Cl |
| $CH_3$ | Cl | Cl | Br |
| $CH_3$ | $NO_2$ | F | H |
| $CH_3$ | $NO_3$ | F | F |
| $CH_3$ | $NO_2$ | F | Cl |
| $CH_3$ | $NO_2$ | F | Br |
| $CH_3$ | $NO_3$ | Cl | H |
| $CH_3$ | $NO_2$ | Cl | F |
| $CH_3$ | $NO_2$ | Cl | Cl |
| $CH_3$ | $NO_2$ | Cl | Br |

Examples of harmful insects against which the compounds of the present invention exhibit remarkable effects include the following:

Harmful insects belonging to Hemiptera:

Planthoppers such as small brown planthopper (*Laodelphax striatellus*), brown plant hopper (*Nilaparvata lugens*), white-backed rice planthopper (*Sogatella furcifera*), etc.; leafhoppers such as green rice leafhopper (*Nephotettix cinticeps*), (*Nephotettix virescens*), etc.; aphids, bugs, whiteflies, scales, lace bugs, psyllids, etc.

Lepidoptera:

Pyralid moths such as rice stem borer (*Chilo suppressalis*), rice leafroller (*Cnaphalocrocis medinalis*), Indian meal moth (*Plodia interpunctella*), etc.; moths such as tobacco cutworm (*Spodoptera litura*), rice armyworm (*Pseudaletia separata*), cabbage armyworm (*Mamestra brassicae*), etc.; Pieridae such as common cabbageworm (*Pieris rapae crucivora*), etc.; Tortricidae or tortricid moths such as *Adoxophyes* spp., *Grapholita* spp., etc.; Carposinidae, lyonetiid moths (Lyonetiidae), tussock moths (Lymantriidae), beet semi-looper (*Autographa nigrisigna*); harmful insects belonging to Agrothis spp. such as turnip cutworm (*Agrothis segetum*), black cutworm (*Agrothis ipsilon*); harmful insects belonging to Hiliothis spp., diamondback moth (*Plutella xylostella*), clothes moths (*Tineidae*), casemaking clothes moth (*Tinea translucens*), webbing clothes moth (*Tineola bisselliella*); etc.

Harmful insects belonging to Diptera:

Mosquitos such as common mosquito (*Culex pipiens pallens*), *Culex tritaeniorhynchus*, etc.; *Aedes* spp. such as *Aedes aeqypti*, *Aedes albopictus*, etc.; *Anopheles* spp. such as *Anopheles sinensis*, etc.; midges (Chironomidae); Muscidae such as housefuly (*Musca domestica*), false stablefly (*Muscina stabulans*), etc.; Calliphoridae; Sarcophagidae; lesser housefly (*Fannia canicularis*); Anthomyiidae or anthomyiid flies such as seedcorn maggot (*Delia platura*), onion maggot (*Delia antiqua*), etc.; fruit flies (Tephritidae); small fruit flies (Drosophilidae); moth flies (Psychodidae); black flies (Simuliidae); Tabanidae; stable flies (Stomoxyidae); etc. Harmful insects belonging to Coleoptera:

Corn root worms such as western corn root-worm (*Diabrotica virgifera*), southern corn root worm (*Diabrotica undecimpunctata*), etc.; scarabs (Scarabaeidae) such as cupreous chafer (*Anomala cuprea*), soybeen beetle (*Anomala rufocuprea*), etc.; weevils such as maize weevil (*Sitophilus zeamais*), rice water weevil (*Lissorhoptrus oryzophilus*), adzuki been weevil (*Callosobruchys chineneis*), etc.; darkling beetles (Tenebrionidae) such as yellow mealworm (*Tenebrio molitor*), red fluor beetle (*Tribolium castaneum*), etc.; leaf beetles (Chrysomelidae) such as cucurbit leaf beetle (*Aulacophora femoralis*), striped flea beetles (*Phyllotreta striolata*), etc.; Anobiidae; Epilachna spp. such as twenty-eight-spotted ladybirds (*Epilachna viqintioctopunctata*), etc.; powderpost beetles (Lyctidae); false powderpost beetles (Bostrychidae), Cerambycidae; robe beetle (*Paederus fusipes*), etc.

Harmful insects belonging to Dictyoptera:

German cockroach (*Blattella germanica*), smokybrown cockroach (*Periplaneta fuliqinosa*), American cockroach (*Periplaneta americana*), brown cockroach (*Periplaneta brunnea*), oriental cockroach (*Blatta orientalis*), etc.

Harmful insects belonging to Thysanoptera:

*Thrips palmi*, flow thrips (*Thrips hawaiiensis*), etc.

Harmful insects belonging to Hymenoptera:

ants (Formicidae); hornets (Vespidae); bethylid wasps (Bethylidae); sawflies (Tenthredinidae) such as cabbage sawfly (*Athalia rosae ruficornis*), etc.

Harmful insects belonging to Orthoptera:

mole crickets (Gryllotalpidae); grasshoppers (Acrididae), etc.;

Harmful insects belonging to Aphaniptera:

*Purex irritans*, etc.

Harmful insects belonging to Anoplura:

*Pediculus humanus capitis, Phthirus pubis,* etc.

Harmful insects belonging to Isoptera:

*Reticulitermes speratus,* Formosan subterranean termite (*Coptotermes formosanus*), etc.

Moreover, the compounds of the present invention are very effective to the insects which develop the resistance against conventional insecticides.

In the case that the compounds of the present invention are used as the active ingredient of insecticidal compositions, the compounds may be used as they are, without adding any other components but in general, the compounds are mixed with a solid carrier, a liquid carrier, a gaseous carrier, a feed, etc. and, if necessary and desired, the mixture is further supplemented with a surfactant and other adjuvants used to prepare insecticidal preparations and prepared into forms such as oil sprays, emulsifiable concentrates, wettable powders, flowable concentrates, granules, dusts, aerosol, fumigants (fogging, etc.), poison bait, etc.

These formulations contain generally 0.01 to 95% by weight of the compounds of the present invention as the active ingredient.

Examples of the solid carrier used for making formulations include fine powders or granulates, etc. of clays (kaolin clay, diatomaceous earth, synthetic hydrated silicon dioxide, bentonite, Fubasami clay terra alba, etc.), talc, ceramics, other inorganic minerals (sericite, quartz, sulfur, activated carbon, calcium carbonate, hydrated silica, etc.), chemical fertilizers (ammonium sulfate, ammonium phosphate, ammonium nitrate, urea, ammonium chloride, etc.), etc. Examples of the liquid carrier include water, alcohols (methanol, ethnaol, etc.), ketones (acetone, methyl ethyl ketone, etc.), aromatic hydrocarbons (benzene, toluene, xylene, ethylbenzene, methylnaphthalene, etc.), aliphatic hydrocarbons (hexane, cyclohexane, kerosene, gas oil, etc.), esters (ethyl acetate, butyl acetate, etc.), nitriles (acetonitrile, isobutyronitrile, etc.), ethers (diisopropyl ether, dioxan, etc.), acid amides (N,N-dimethylformamide, N,N-dimethylacetamide, etc.), halogenated hydrocarbons (dichloromethane, trichloroethane, carbon tetrachloride, etc.), dimethylsulfoxide; vegetable oils such as soybean oil, cotton seed oil, etc. Examples of the gaseous carrier, i.e., propellant, include freon gas, butane gas, LPG (liquefied petroleum gas), dimethyl ether, carbon dioxide, etc.

Examples of the surfactant include alkyl sulfates, alkyl sulfonic acid salts, alkylaryl sulfonic acid salts, alkyl aryl ethers and polyoxyethylene derivatives thereof, polyethylene glycol ether, polyvalent alcohol esters, sugar alcohol derivatives, etc.

Examples of the adjuvants such as binders, dispersing agents, etc. for formulations include casein, gelatin, polysaccharides (starch powders, gum arabic, cellulose derivatives, alginic acid, etc.), lignin derivatives, bentonite, sugars, synthetic water-soluble high molecular substances (polyvinyl alcohol, polyvinylpyrrolidone, polyacrylic acid, etc.). Examples of the stabilizer include PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids or esters thereof, and the like.

As a base material for the poison baits, there are, for example, feed components such as crop powders, essential vegetable oil, sugars, crystalline cellulose etc.; antioxidants such as dibutylhydroxytoluene, nordihyroguaiaretic acid, etc.; preservatives such as dehydroacetic acid, etc.; feeding error preventing agents such as red pepper powders, etc.; incentive flavor such as cheese flavor, onion flavor, etc.

The thus obtained formulations may be used as they are or after diluting with water, etc. Alternatively, the formulations may be used as admixture with other insecticides, nematocides, acaricides, bacteriocides, herbicides, plant growth regulators, synergistic agents, fertilizers, soil conditioners, animal feed, etc., or may also be used simultaneously with them, without mixing therewith.

Where the compounds of the present invention are used as insecticides for agricultural use, the dose is generally 0.1 g to 100 g per 10 ares; when emulsifiable concentrates, wettable powders, flowable concentrates, etc. are used after diluting them with water, the concentration is 0.1 ppm to 500 ppm. Granules, dusts, etc. may be used as they are, without diluting them. For purposes of household and public hygiene, emulsifiable concentrates, wettable powders, flowable concentrates, etc. are diluted with water in a concentration of 0.1 ppm to 500 ppm; oils, aerosol, fumigants, poison baits, etc. may be used as they are.

These doses and concentrations may vary depending upon kind of formulations, timing for application, place applied, method for application, kinds of insect, condition of damages, etc. and may be increased or decreased, irrespective of the ranges set forth above.

Hereafter the present invention is described in more detail, by referring to synthesis examples, formulation examples and test examples but is not deemed to these examples.

SYNTHESIS EXAMPLE 1 (SYNTHESIS OF COMPOUND NO. (10))

To a solution of 0.41 g (2 mmol) of 4(5)-(2-chloro-1,1,2,2-tetrafluoroethyl)imidazole in 5 ml of N,N-dimethylformamide was added 80 mg (2 mmol) of an oily sodium hydride (60%) while cooling with ice, followed by stirring at the same temperature for 10 minutes. After the reaction was completed, to the reaction mixture was added dropwise 0.50 g (2 mmol) of 3,4,5-trichlorobenzotrifluoride, followed by stirring at 80°–90° C. for 7 hours. After the reaction was completed, the reaction mixture was poured into water, and extracted with ethyl acetate. Further, then the residue was washed with brine, dried over magnesium sulfate, and concentrated under reduced pressure. The obtained product was subjected to silica gel chromatography to give 0.23 g of 1-(2,6-dichloro-4-trifluoromethylphenyl)-4-(2-chloro-1,1,2,2-tetrafluoroethyl)imidazole.

m.p. 101.2° C.

SYNTHESIS EXAMPLE 2 (SYNTHESIS OF COMPOUND NO. (23))

To a solution of 0.43 g (2 mmol) of 2-methyl-4(5)-(2-chloro-1,1,2,2-tetrafluoroethyl)imidazole in 5 ml of N,N-dimethylformamide was added both of 0.41 g (3 mmol) of anhydrous potassium carbonate and 0.47 g (2 mmol) of 3,5-dichloro-4-fluorobenzotrifluoride, followed by stirring at 80°–90° C. for 7 hours. After cooling the reaction mixture was poured into water, and extracted with ethyl acetate. Further, then the residue was washed with brine, dried over magnesium sulfate, and concentrated under reduced pressure. The obtained product was subjected to silica gel chromatography to give 0.33 g of 1-(2,6-dichloro-4-trifluoromethylphenyl)-2-methyl-4-(2-chloro-1,1,2,2-tetrafluoroethyl)imidazole.

m.p. 134.3° C.

Examples of the present invention prepared in the same manner as above are shown in Table 2.

TABLE 2

$$\text{[I]}$$

Structure: CF$_3$-substituted benzene ring with X and Y substituents, N-linked to an imidazoline-type ring bearing R and CF$_2$CF$_2$Z.

| Compound No. | R | X | Y | Z | Physical constant |
|---|---|---|---|---|---|
| (1) | H | F | F | H | m.p. 61–62° C. |
| (2) | H | F | F | F | m.p. 72.5° C. |
| (3) | H | F | F | Br | m.p. 70.9° C. |
| (4) | H | F | Cl | H | m.p. 62–64° C. |
| (5) | H | F | Cl | F | m.p. 66.3° C. |
| (6) | H | F | Cl | Cl | $n_D^{23.3}$ 1.4620 |
| (7) | H | F | Cl | Br | m.p. 51.7° C. |
| (8) | H | Cl | Cl | H | m.p. 67.6° C. |
| (9) | H | Cl | Cl | F | m.p. 88.8° C. |
| (10) | H | Cl | Cl | Cl | m.p. 101.2° C. |
| (11) | H | Cl | Cl | Br | m.p. 91.6° C. |
| (12) | H | NO$_2$ | Cl | H | $n_D^{23.8}$ 1.4868 |
| (13) | H | NO$_2$ | Cl | F | m.p. 95.3° C. |
| (14) | H | NO$_2$ | Cl | Br | m.p. 94.4° C. |
| (15) | CH$_3$ | F | F | F | m.p. 99–100° C. |
| (16) | CH$_3$ | F | F | Br | m.p. 65–66° C. |
| (17) | CH$_3$ | F | Cl | H | m.p. 87.2° C. |
| (18) | CH$_3$ | F | Cl | F | m.p. 123.3° C. |
| (19) | CH$_3$ | F | Cl | Cl | m.p. 179.0° C. |
| (20) | CH$_3$ | F | Cl | Br | m.p. 92.2° C. |
| (21) | CH$_3$ | Cl | Cl | H | m.p. 104.0° C. |
| (22) | CH$_3$ | Cl | Cl | F | m.p. 138.3° C. |
| (23) | CH$_3$ | Cl | Cl | Cl | m.p. 134.3° C. |
| (24) | CH$_3$ | Cl | Cl | Br | m.p. 122.0° C. |
| (25) | CH$_3$ | NO$_2$ | Cl | H | m.p. 114.4° C. |
| (26) | CH$_3$ | NO$_2$ | Cl | F | m.p. 123.9° C. |
| (27) | CH$_3$ | NO$_2$ | Cl | Br | m.p. 144.8° C. |

Next, Formulation examples are shown, wherein parts are all by weight and the compounds of the present invention are designated by the compound numbers shown in Table 2.

FORMULATION EXAMPLE 1

Emulsifiable Concentrate

After 10 parts each of Compounds (1) through (27) of the present invention are dissolved in 35 parts of xylene and 35 parts of dimethylformamide, 14 parts of polyoxyethylene styrylphenyl ether and 6 parts of calcium dodecylbenzenesulfonate are added to the solutions. The resulting mixtures are thoroughly mixed stirred to give 10% emulsifiable concentrate, respectively.

FORMULATION EXAMPLE 2

Wettable Powder

After 20 parts of Compound (1) through (27) of the present invention are added to a mixture of 4 parts of sodium laurylsulfate, 2 parts of calcium lignisulfonate, 20 parts of synthetic hydrated silicon dioxide fine powders and 54 parts of diatomaceous earth, the mixture is mixed and stirred with a juice mixer to give 20% wettable powder.

FORMULATION EXAMPLE 3

Granule

After 5 parts of synthetic hydrated silicon dioxide fine powders, 5 parts of sodium dodecylbenzenesulfonate, 30 parts of bentonite and 55 parts of clay are added to 5 parts of Compound (1) through (27) of the present invention, the mixture is thoroughly mixed and stirred. A suitable amount of water is further added to the mixture followed by stirring. The mixture is granulated with a granulator and air-dried to give 5% granule.

FORMULATION EXAMPLE 4

Dust

After 1 part of Compound (22) of the present invention is dissolved in a appropriate amount of acetone, 5 parts of synthetic hydrated silicon dioxide fine powders, 0.3 parts of PAP and 93.7 parts of clay are added to the solution. The mixture is mixed and stirred with a juice mixer and acetone is evaporated off to give 1% dust.

FORMULATION EXAMPLE 5

Flowable concentrate

After 20 parts of Compound (23) of the present invention and 1.5 part of sorbitan trioleate are mixed with 28.5 parts of an aqueous solution containing 2 parts of polyvinyl alcohol, the mixture is finely divided (less than 3μ in particle diameter) with a sand grinder. Then, 40 parts of aqueous solution containing 0.05 part of xanthane gum and 0.1 part of aluminum magnesium silicate are added to the powders and 10 parts of propylene glycol are further added thereto. The mixture is thoroughly mixed and stirred to give 20% flowable concentrate for aqueous suspension.

FORMULATION EXAMPLE 6

Oil spray

After 0.1 part of Compound (1) through (27) of the present invention is dissolved in 5 parts of xylene and 5 parts of trichloroethane, the solution is mixed with 89.9 parts of deodorized kerosene to give 0.1% oil spray.

FORMULATION EXAMPLE 7

Oil-based aerosol

After 0.1 part of Compound (1) through (27) of the present invention, 0.2 part of tetramethrin, 0.1 part of d-phenothrin, 10 parts of trichloroethane and 59.6 parts of deodorized kerosene are mixed with each other and dissolved. The solution is filled in an aerosol container. After a valve is mounted to the container, 30 parts of propellant (liquefied petroleum gas) are filled under pressure through the valve to give oil-based aerosol.

FORMULATION EXAMPLE 8

Water-based aerosol

After 0.2 part of Compound (24) of the present invention, 0.2 part of d-allethrin, 0.2 part of d-phenothrin, 5 parts of xylene, 3.4 parts of deodorized kerosene and 1 part of emulsifier [ATMOS 300 (registered trademark, Atlas Chemical Co., Ltd.)] are mixed with each other and dissolved. The solution and 50 parts of distilled water are filled in an aerosol container. After a valve is mounted to the container, 40 parts of propellant (liquefied petroleum gas) are filled under pressure through the valve to give water-based aerosol.

FORMULATION EXAMPLE 9

Mosquito coil

After 0.3 part of d-allethrin is added to 0.3 g of Compound (20) of the present invention, the mixture is dissolved in 20 ml of acetone. The solution is then uniformly mixed with 99.4 g of carrier for mosquito-=coil (taba powder:sake lees powder:wood powder of 4:3:3) with stirring and 120 ml of water is then added to the mixture. The mixture is thoroughly kneaded, molded and dried to give mosquito-coil.

FORMULATION EXAMPLE 10

Electric mosquito mat

Acetone is added to 0.4 g of Compound (19) of the present invention, 0.4 g of d-allethrin and 0.4 g of piperonyl butoxide to dissolve and make the whole volume 10 ml. This solution, 0.5 ml, is uniformly impregnated with a base material for electric mat (a mixture of cotton linter and pulp solidified in a plate-like form) having 2.5 cm × 1.5 cm and a thickness of 0.3 cm to give an electric mosquito mat.

FORMULATION EXAMPLE 11

Fumigant

After 100 mg of Compound (16) of the present invention is dissolved in a appropriate amount of acetone, the solution is impregnated with a porous ceramic plate having 4.0 cm × 4.0 cm and a thickness of 1.2 cm to give a fumigant.

FORMULATION EXAMPLE 12

Poison bait

After 10 mg of Compound (1) through (27) of the present invention is dissolved in a 0.5 ml acetone, the solution is applied to 5 g of the powder of dry animal food. The powder is dried to give a 0.5% poison bait.

Next, effectiveness of the compounds of the present invention a the active ingredient of insecticidal compositions is described below, with reference to test examples, wherein the compounds of the present invention are designated by the compound numbers shown in Table 2 and compounds used for comparison and control are designated by the compound numbers shown in Table 3.

TABLE 3

| Compound Symbol | Chemical Structure | Note |
|---|---|---|
| (A) | [structure: pyrimidine with CH$_3$, C$_4$H$_9$-tert, N-C(=O)-N(CH$_3$)$_2$] | Compound described in U.S. Pat. No. 3,868,458 and 3,940,484 |
| (B) | [structure: pyrimidine with CH$_3$S, C$_4$H$_9$-tert, N-C(=O)-N(CH$_3$)$_2$] | Compound described in U.S. Pat. No. 3,996,366 |
| (C) | [structure: 2-F, 4-CF$_3$, 6-Cl phenyl attached to imidazole with CF$_3$] | Compound unknown to the literatures m.p. 89.1° C. |
| (D) | [structure: 2-F, 4-CF$_3$, 6-Cl phenyl attached to imidazole with CH$_3$ and CF$_3$] | Compound unknown to the literatures m.p. 80.6° C. |
| (E) | [structure: 2-F, 4-CF$_3$, 6-Cl phenyl attached to imidazole with CF$_2$CF$_2$CF$_3$] | Compound unknown to the literatures $n_D^{25.5}$ 1.4314 |

TABLE 3-continued

| Compound Symbol | Chemical Structure | Note |
|---|---|---|
| (F) | 2-fluoro-4-(trifluoromethyl)-6-chloro-N-[1-methyl-3-(heptafluoropropyl)-prop-2-enylidene]aniline structure with CF₃, F, Cl substituents on benzene ring, N=C(CH₃)–CH=C(CF₂CF₂CF₃) | Compound unknown to the literatures m.p. 79.7° C. |
| (G) | Similar aniline structure with CF₃, F, Cl on benzene ring, N=C(CH₃)–CH=C(CF₂CF₂CF₂CF₃) | Compound unknown to the literatures $n_D^{24.7}$ 1.4213 |

TEST EXAMPLE 1 (INSECTICIDAL TEST ON NYMPHS OF BROWN PLANTHOPPER)

The emulsifiable concentrate of the test compound prepared according to Formulation Example 1 was diluted with water (corresponding to 500, 5 or 0.5 ppm) and a rice plant seedling (length of about 12 cm) was immersed in the dilution for a minute. After air-drying, the rice plant seedling was put in a test tube and about 30 nymphs of brown planthopper (*Nilaparvata lugens*) were released. Six days after, the nymphs were observed if they were alive or dead. Criterion for the judgement is as follows.

a: no insect was alive.
b: alive insects were 5 or less.
c: alive insects were 6 or more.

The results are shown in Table 4.

TABLE 4

| Test Compound | Concentration (ppm) | Efficacy |
|---|---|---|
| (1) | 500 | a |
| | 5 | a |
| | 0.5 | a |
| (2) | 500 | a |
| | 5 | a |
| | 0.5 | a |
| (3) | 500 | a |
| | 5 | a |
| | 0.5 | a |
| (4) | 500 | a |
| | 5 | a |
| | 0.5 | a |
| (5) | 500 | a |
| | 5 | a |
| | 0.5 | a |
| (6) | 500 | a |
| | 5 | a |
| | 0.5 | a |
| (7) | 500 | a |
| | 5 | a |
| | 0.5 | a |
| (8) | 500 | a |
| | 5 | a |
| | 0.5 | a |
| (9) | 500 | a |
| | 5 | a |
| | 0.5 | a |
| (10) | 500 | a |
| | 5 | a |
| | 0.5 | a |
| (11) | 500 | a |
| | 5 | a |
| | 0.5 | a |
| (12) | 500 | a |
| (13) | 500 | a |
| (14) | 500 | a |
| (15) | 500 | a |
| | 5 | a |
| | 0.5 | a |
| (16) | 500 | a |
| | 5 | a |
| | 0.5 | a |
| (17) | 500 | a |
| | 5 | a |
| | 0.5 | a |
| (18) | 500 | a |
| | 5 | a |
| | 0.5 | a |
| (19) | 500 | a |
| | 5 | a |
| | 0.5 | a |
| (20) | 500 | a |
| | 5 | a |
| | 0.5 | a |
| (21) | 500 | a |
| | 5 | a |
| | 0.5 | a |
| (22) | 500 | a |
| | 5 | a |
| | 0.5 | a |
| (23) | 500 | a |
| | 5 | a |
| | 0.5 | a |
| (24) | 500 | a |
| | 5 | a |
| | 0.5 | a |
| (25) | 500 | a |
| | 5 | a |
| | 0.5 | a |
| (26) | 500 | a |
| | 5 | a |
| | 0.5 | a |
| (27) | 500 | a |
| | 5 | a |
| | 0.5 | a |
| Untreated | | c |

TEST EXAMPLE 2 (INSECTICIDAL TEST ON SOUTHERN CORN ROOTWORM)

On the bottom of a polyethylene cup having a diameter of 5.5 cm, a filter paper which is of the same size was laid down and 1 ml of an aqueous dilution (500 or 50 ppm) of the emulsifiable concentrate of the test compound prepared according to Formulation Example 1 was dropped onto the filter paper and one corn sprout was put as feed. About 30 eggs of southern corn rootworm (*Diabrotica undecimpunctata*) were put in the cup. Eight days after the cup was covered, dead or alive larvae hatched were examined. Criterion for the judgement is as follows.

a: no insect was alive.
b: alive insects were 5 or less.
c: alive insects were 6 or more.

The results are shown in Table 5.

TABLE 5

| Test Compound | Concentration (ppm) | Efficacy |
|---|---|---|
| (1) | 500 | a |
|  | 50 | a |
| (2) | 500 | a |
|  | 50 | a |
| (3) | 500 | a |
|  | 50 | a |
| (4) | 500 | a |
|  | 50 | a |
| (5) | 500 | a |
|  | 50 | a |
| (6) | 500 | a |
|  | 50 | a |
| (7) | 500 | a |
|  | 50 | a |
| (8) | 500 | a |
|  | 50 | a |
| (9) | 500 | a |
|  | 50 | a |
| (10) | 500 | a |
|  | 50 | a |
| (11) | 500 | a |
|  | 50 | a |
| (12) | 500 | a |
|  | 50 | a |
| (13) | 500 | a |
|  | 50 | a |
| (14) | 500 | a |
|  | 50 | a |
| (15) | 500 | a |
|  | 50 | a |
| (16) | 500 | a |
|  | 50 | a |
| (17) | 500 | a |
|  | 50 | a |
| (18) | 500 | a |
|  | 50 | a |
| (19) | 500 | a |
|  | 50 | a |
| (20) | 500 | a |
|  | 50 | a |
| (21) | 500 | a |
|  | 50 | a |
| (22) | 500 | a |
|  | 50 | a |
| (23) | 500 | a |
|  | 50 | a |
| (24) | 500 | a |
|  | 50 | a |
| (25) | 500 | a |
|  | 50 | a |
| (26) | 500 | a |
|  | 50 | a |
| (27) | 500 | a |
|  | 50 | a |
| Untreated |  | c |

TEST EXAMPLE 3 (INSECTICIDAL TEST ON SOUTHERN CORN ROOTWORM)

Five milliliters of an aqueous dilution of an emulsifiable concentrate of the test compound prepared according to Formulation Example 1 was mixed with 50 g of a 16 mesh soil. The concentration of the active ingredient in the soil was controlled to 0.25 or 0.125 ppm.

Each of the soils was packed into a polyethylene cup having a diameter of 5.6 cm and a height of 5.8 cm, into which were planted two seeds of maize of which root had grown up to a length of 2-3 cm. Then, 10 third-instar larvae of southern corn rootworm (*Diabrotica undecimpunctata howardi*) were allowed to live in the cup. Two days later, the numbers of controlled insects (dead and moribund) and uncontrolled insects (vigor) were counted for efficacy (%). The results are shown in Table 6.

TABLE 6

| Test Compound | Concentration (ppm) | Efficacy (%) |
|---|---|---|
| (5) | 0.25 | 100 |
|  | 0.125 | 100 |
| (18) | 0.25 | 100 |
|  | 0.125 | 100 |
| (C) | 0.25 | 0 |
|  | 0.125 | 0 |
| (D) | 0.25 | 0 |
|  | 0.125 | 0 |
| (E) | 0.25 | 10 |
|  | 0.125 | 0 |
| (F) | 0.25 | 0 |
|  | 0.125 | 0 |
| (G) | 0.25 | 0 |
|  | 0.125 | 0 |
| Untreated |  | 0 |

TEST EXAMPLE 4 (INSECTICIDAL TEST ON COMMON MOSQUITO)

The emulsifiable concentrate of the test compound prepared according to Formulation Example 1 was diluted with water and 0.7 ml of the dilution was added to 100 ml of ion exchange water (concentration of the effective ingredient was 3.5 ppm). In the mixture were released 20 last instar larvae of common mosquito (*Culex pipiens pallens*). One day after the release, mortality was examined.

Criterion for the judgement is as follows.
a: 90% or more
b: not less than 10% but less than 90%
c: less than 10%

The results are shown in Table 7.

TABLE 7

| Test Compound | Efficacy |
|---|---|
| (1) | a |
| (2) | a |
| (3) | a |
| (4) | a |
| (5) | a |
| (6) | a |
| (7) | a |
| (8) | a |
| (9) | a |
| (10) | a |
| (11) | a |
| (12) | a |
| (13) | a |
| (14) | a |
| (15) | a |
| (16) | a |
| (17) | a |
| (18) | a |
| (19) | a |
| (20) | a |
| (21) | a |
| (22) | a |
| (23) | a |
| (24) | a |
| (25) | a |
| (26) | a |
| (27) | a |

TABLE 7-continued

| Test Compound | Efficacy |
| --- | --- |
| Untreated | c |

TEST EXAMPLE 5 (INSECTICIDAL TEST ON GERMAN COCKROACH)

On the bottom of a polyethylene cup having a diameter of 5.5 cm, a filter paper which is of the same size was laid down and 0.7 ml of an aqueous dilution (500 ppm) of the emulsifiable concentrate of the test compound prepared according to Formulation Example 1 was dropped onto the filter paper. As feed, 30 mg of sucrose was uniformly spread thereon. In the cup, 10 adult males of German cockroach (*Blattella germanica*) were released. Six days after the cup was covered, dead or alive insects were examined to determine mortality.

The results are shown in Table 8.

TABLE 8

| Test Compound | Mortality (%) 500 ppm |
| --- | --- |
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (13) | 100 |
| (14) | 100 |
| (15) | 100 |
| (16) | 100 |
| (17) | 100 |
| (18) | 100 |
| (19) | 100 |
| (20) | 100 |
| (21) | 100 |
| (22) | 100 |
| (23) | 100 |
| (24) | 100 |
| (25) | 100 |
| (26) | 100 |
| (27) | 100 |
| (A) | 0 |
| (B) | 0 |
| Untreated | 0 |

TEST EXAMPLE 6 (INSECTICIDAL TEST ON HOUSEFLY)

On the bottom of a polyethylene cup having a diameter of 5.5 cm, a filter paper which is of the same size was laid down and 0.7 ml of an aqueous dilution (500 ppm) of the emulsifiable concentrate of the test compound prepared according to Formulation Example 1 was dropped onto the filter paper. As feed, 30 mg of sucrose was uniformly spread thereon. In the cup, 10 adult females of housefly (*Musca domestica*) were released. Fourty eight hours after the cup was covered, dead or alive insects were examined to determine mortality (2 replications). The results are shown in Table 9.

TABLE 9

| Test Compound | Mortality (%) 500 ppm |
| --- | --- |
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (13) | 100 |
| (14) | 100 |
| (15) | 100 |
| (16) | 100 |
| (17) | 100 |
| (18) | 100 |
| (19) | 100 |
| (20) | 100 |
| (21) | 100 |
| (22) | 100 |
| (23) | 100 |
| (24) | 100 |
| (25) | 100 |
| (26) | 100 |
| (27) | 100 |
| Untreated | 0 |

What is claimed is:

1. A 1-phenylimidazole derivative having the formula:

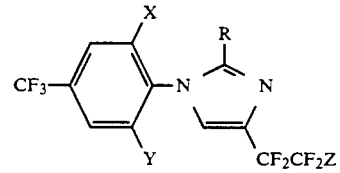

wherein R is a hydrogen atom or a methyl group; X is a fluorine atom, a chlorine atom or a nitro group; Y is a fluorine atom or a chlorine atom; Z is a hydrogen atom, a fluorine atom, a chlorine atom or a bromine atom.

2. A 1-phenylimidazole derivative according to claim 1, which is 1-(2,6-difluoro-4-trifluoromethylphenyl)-4-(1,1,2,2-tetrafluoroethyl)imidazole.

3. A 1-phenylimidazole derivative according to claim 1, which is 1-(2,6-difluoro-4-trifluoromethylphenyl)-4-pentafluoroethylimidazole.

4. A 1-phenylimidazole derivative according to claim 1, which is 1-(2,6-difluoro-4-trifluoromethylphenyl)-4-(2-bromo-1,1,2,2-tetrafluoroethyl)imidazole.

5. A 1-phenylimidazole derivative according to claim 1, which is 1-(2-chloro-6-fluoro-4-trifluoromethylphenyl)-4-(1,1,2,2-tetrafluoroethyl)imidazole.

6. A 1-phenylimidazole derivative according to claim 1, which is 1-(2-chloro-6-fluoro-4-trifluoromethylphenyl)-4-pentafluoroethylimidazole.

7. A 1-phenylimidazole derivative according to claim 1, which is 1-(2-chloro-6-fluoro-4-trifluoromethylphenyl)-4-(2-chloro-1,1,2,2-tetrafluoroethyl) imidazole.

8. A 1-phenylimidazole derivative according to claim 1, which is 1-(2-chloro-6-fluoro-4-trifluoromethylphenyl)-4-(2-bromo-1,1,2,2-tetrafluoroethyl) imidazole.

9. A 1-phenylimidazole derivative according to claim 1, which is 1-(2,6-dichloro-4-trifluoromethylphenyl)-4-(1,1,2,2-tetrafluoroethyl)imidazole.

10. A 1-phenylimidazole derivative according to claim 1, which is 1-(2,6-dichloro-4-trifluoromethylphenyl)-4-pentafluoroethylimidazole.

11. A 1-phenylimidazole derivative according to claim 1, which is 1-(2,6-dichloro-4-trifluoromethylphenyl)-4-(2-chloro-1,1,2,2-tetrafluoroethyl)imidazole.

12. A 1-phenylimidazole derivative according to claim 1, which is 1-(2,6-dichloro-4-trifluoromethylphenyl)-4-(2-bromo-1,1,2,2-tetrafluoroethyl)imidazole.

13. A 1-phenylimidazole derivative according to claim 1, which is 1-(2,6-dichloro-4-trifluoromethylphenyl)-2-methyl-4-pentafluoroethylimidazole.

14. A 1-phenylimidazole derivative according to claim 1, which is 1-(2,6-dichloro-4-trifluoromethylphenyl)-2-methyl-4-(2-bromo-1,1,2,2-tetrafluoroethyl)imidazole.

15. A 1-phenylimidazole derivative according to claim 1, which is 1-(2-chloro-6-fluoro-4-trifluoromethylphenyl)-2-methyl-4-(1,1,2,2-tetrafluoroethyl)imidazole.

16. A 1-phenylimidazole derivative according to claim 1, which is 1-(2-chloro-6-fluoro-4-trifluoromethylphenyl)-2-methyl-4-pentafluoroethylimidazole.

17. A 1-phenylimidazole derivative according to claim 1, which is 1-(2-chloro-6-fluoro-4-trifluoromethylphenyl)-2-methyl-4-(2-chloro-1,1,2,2-tetrafluoroethyl)imidazole.

18. A 1-phenylimidazole derivative according to claim 1, which is 1-(2-chloro-6-fluoro-4-trifluoromethylphenyl)-2-methyl-4-(2-bromo-1,1,2,2-tetrafluoroethyl)imidazole.

19. A 1-phenylimidazole derivative according to claim 1, which is 1-(2,6-dichloro-4-trifluoromethylphenyl)-2-methyl-4-(1,1,2,2-tetrafluoroethyl)imidazole.

20. A 1-phenylimidazole derivative according to claim 1, which is 1-(2,6-dichloro-4-trifluoromethylphenyl)-2-methyl-4-pentafluoroethylimidazole.

21. A 1-phenylimidazole derivative according to claim 1, which is 1-(2,6-dichloro-4-trifluoromethylphenyl)-2-methyl-4-(2-chloro-1,1,2,2-tetrafluoroethyl)imidazole.

22. A 1-phenylimidazole derivative according to claim 1, which is 1-(2,6-dichloro-4-trifluoromethylphenyl)-2-methyl-4-(2-bromo-1,1,2,2-tetrafluorothyl)imidazole.

23. An insecticidal composition which comprises an insecticidally effective amount of the 1-phenylimidazole derivative according to claim 1 and an inert carrier.

24. A method for controlling insect pests which comprises applying an insecticidally effective amount of the 1-phenylimidazole derivative according to claim 1 to the insect pests or to the locus where insect pests propagate.

* * * * *